United States Patent [19]

Aoyagi

[11] 4,365,989
[45] Dec. 28, 1982

[54] 2-THIOCYANOMETHYLTHIO-4,4-DIALKYL-5-SUBSTITUTED-THIAZOLINE FUNGICIDES

[75] Inventor: Edward I. Aoyagi, Petaluma, Calif.

[73] Assignee: Chevron Research Company, San Francisco, Calif.

[21] Appl. No.: 343,089

[22] Filed: Jan. 27, 1982

[51] Int. Cl.³ .............. C07D 277/08; A61K 31/245; A01N 43/02
[52] U.S. Cl. .............................. 71/67; 71/90; 424/270; 548/186
[58] Field of Search .................. 548/186; 424/270; 71/67, 90

[56] References Cited

U.S. PATENT DOCUMENTS 3,463,785 8/1969 Buckman .................. 548/169
4,335,133 6/1982 Aoyagi ..................... 424/270

Primary Examiner—Robert Gerstl
Attorney, Agent, or Firm—D. A. Newell; T. G. De Jonghe; L. S. Squires

[57] ABSTRACT

Compounds of the formula:

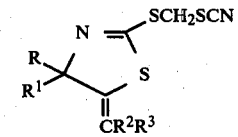

wherein R and $R^1$ are independently lower alkyl or R and $R^1$ are joined to form a cycloalkyl group of 5 to 8 carbon atoms; $R^2$ is hydrogen or chloro; and $R^3$ is hydrogen, halogen or $-SR^4$ wherein $R^4$ is lower alkyl, phenyl or phenyl substituted with 1 to 3 of the same or different substituents selected from halogen, nitro, lower alkyl or lower alkyl substituted with 1 to 3 halogens with the proviso that when $R^2$ is chloro, $R^3$ is not $-SR^4$, bromo, fluorine or iodine, possess good fungicidal activity. Moreover, some of the compounds of this invention are active as algicides and herbicides.

15 Claims, No Drawings

2-THIOCYANOMETHYLTHIO-4,4-DIALKYL-5-SUBSTITUTED-THIAZOLINE FUNGICIDES

BACKGROUND OF THE INVENTION

This invention is drawn to novel fungicides. With the world more and more dependent for food on increasingly less acreage of cultivated land, it is necessary to develop fungicides which effectively protect crops from fungicidal destruction.

Azerbaev et al. disclose 2-benzylamino-4,4-dialkyl-5-methylene-1,3-thiazolines in Chem. Abstracts 79:66237v (1973).

Eloy et al. disclose 2-alkylamino-5-methylenethiazoles in Chem. Abstracts 81:13439x (1974).

U.S. patent applications Ser. Nos. 115,654 and 204,437 disclose 2-arylthio or arylamino-4,4-dialkyl-5-methylene-1,3-thiazoles possessing bacteriocidal activity.

U.S. patent application Ser. No. 115,593 discloses 2-amino-substituted-5-methylenethiazole and 3-amino-substituted-1-methylene-2,4-thiazaspiro[5.4]decane as herbicidal.

Danish Pat. No. 104,103 discloses thiazoline compounds possessing fungicidal, insecticidal and bacteriocidal activity.

SUMMARY OF THE INVENTION

The compounds of the present invention are represented by the formula

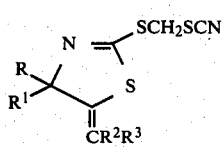

wherein R and $R^1$ are independently lower alkyl or R and $R^1$ are joined to form a cycloalkyl group of 5 to 8 carbon atoms; $R^2$ is hydrogen or chloro; $R^3$ is hydrogen, halogen or $-SR^4$ wherein $R^4$ is lower alkyl, phenyl or phenyl substituted with 1 to 3 of the same or different substituents selected from fluoro, chloro, bromo, iodo, nitro, lower alkyl or lower alkyl substituted with 1 to 3 halogens with the proviso that when $R^2$ is chloro, $R^3$ is not $-SR^4$, bromine, fluorine or iodine.

Preferred R and $R^1$ lower alkyl groups include methyl, ethyl and n-propyl.

Preferred R and $R^1$ cycloalkyl groups include cyclohexyl.

Preferred $R^3$ groups include chloro, bromo, hydrogen, or 4-chlorophenylthio.

Among other factors the present invention is based on my finding that the compounds of this invention are surprisingly good fungicides. In particular, some of the compounds of this invention are especially effective against Grape Downy Mildew. Moreover, some of the compounds of this invention are active as algicides and herbicides.

DEFINITIONS

As used herein the following terms have the following meanings unless expressly stated to the contrary. The term "alkyl" refers to both straight- and branched-chain alkyl groups. The term "lower alkyl" refers to both straight- and branched-chain alkyl groups having a total of 1 through 6 carbon atoms and includes primary, secondary and tertiary alkyl groups. Typical lower alkyls include, for example, methyl, ethyl, n-propyl, isopropyl, n-butyl, t-butyl and the like.

The term "cycloalkyl" refers to the group

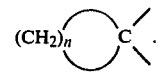

The term cycloalkyl of 5 to 8 carbons includes cyclopentyl, cyclohexyl, cycloheptyl and cyclooctyl.

The term "thiazoline" refers to the group:

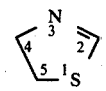

with the conventional numbering system included therein.

The term "5-methylenethiazoline" refers to the group:

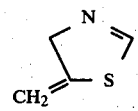

The term "5-substituted methylenethiazoline" refers to the group:

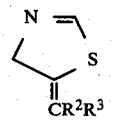

where $R^2$ and $R^3$ are as defined above.

The term "thiocyanomethylthio" refers to the group: $-SCH_2SCN$. Thus the term "2-thiocyanomethylthio-5-methylenethiazoline" refers to the group:

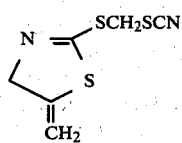

DETAILED DESCRIPTION OF THE INVENTION

The compounds of the present invention are prepared according to the synthetic scheme shown below:

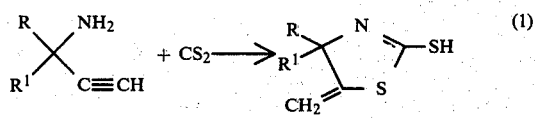

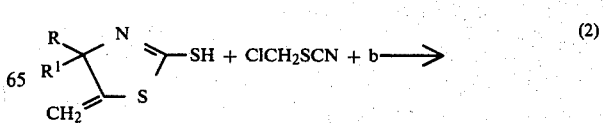

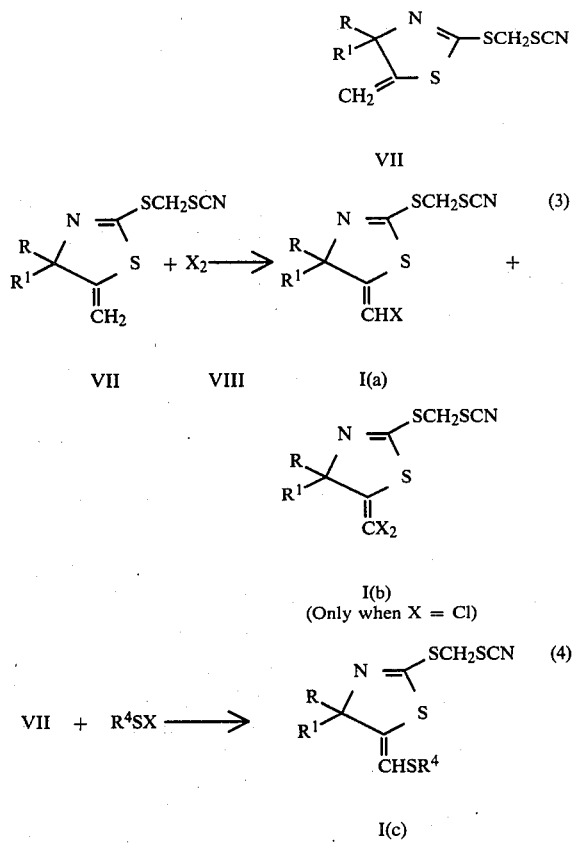

wherein R, $R^1$ and $R^4$ are as defined above, X is halogen and b is a base.

Reaction (1) is a conventional condensation reaction and may be performed by reacting essentially equimolar amounts of the amino propargyl compound, II, with carbon disulfide to form the thiazoline intermediate, IV. Preferably, because of the higher yield of IV, reaction (1) is conducted by reacting the amino propargyl compound with 4 equivalents of carbon disulfide plus a catalytic amount of pyridine hydrochloride. The reaction is conducted in the liquid phase using an inert organic solvent such as chloroform, carbon tetrachloride, ether, dimethoxyethane and the like. The reaction is generally conducted at from 0°–100° C. Preferably the reaction is conducted at from 30°–50° C. Reaction pressure is not critical and for convenience the reaction is generally conducted at atmospheric pressure. The reaction is generally complete within 1 to 72 hours. The product, IV, is then isolated by conventional procedures such as extraction, filtration, chromatography, distillation or alternatively is used in reaction 2 without purification and/or isolation.

Reaction (2) is conducted by adding an essentially equimolar amount or a slight excess thereof of an organic or inorganic base to the thiazoline intermediate, IV. Suitable bases include for instance, sodium hydride, triethylamine, pyridine and the like, although preferably sodium hydride is employed. The addition is done in the liquid phase employing an inert organic solvent such as ethyl acetate, toluene, dimethoxyethane, diethyl ether and the like. After addition of the base, an essentially equimolar amount of chloromethyl thiocyanate, V, is added to the system. The reaction is generally conducted at from 0° to 100° C. although preferably the reaction is conducted at 15° to 20° C. Reaction pressure is not critical and for convenience the reaction is generally conducted at atmospheric pressure. The reaction is generally complete within 1 to 24 hours. The product, VII, is then isolated by conventional procedures such as extraction, filtration, chromatography, distillation or alternatively is used in either reaction (3) or (4) without purification and/or isolation.

Reaction (3) is conducted by adding an essentially equimolar amount of a halogen, VIII, to VII, to give the monohalosubstituted vinyl compound, Ia. The reaction is conducted in the liquid phase using an inert organic solvent such as chloroform, methylene chloride, and the like. Optionally, an essentially equimolar amount of an organic or inorganic base may be added to scavenge the acid generated in the reaction. Alternatively and preferably, the system may be washed with an excess of an aqueous basic solution after reaction completion to remove the acid generated during the reaction. Suitable bases which may be employed include sodium carbonate, potassium carbonate, sodium bicarbonate and the like. The reaction is generally conducted at from 0° to 100° C. although preferably at from 15° to 20° C. Reaction pressure is not critical and for convenience the reaction is generally conducted at atmospheric pressure. The reaction is generally complete from within 1 to 24 hours. The product, I(a), is then isolated by conventional procedures such as extraction, filtration, chromatography, distillation and the like.

The 1,1-dichlorovinyl product, I(b), may be prepared by adding 2 equivalents of chlorine to VII. The reaction is conducted in the same manner as described above as reaction (3), except that 2 equivalents of a base will be required to scavenge the acid generated. The product, I(b), is isolated by conventional procedures such as extraction, filtration, chromatography, distillation and the like.

Reaction (4) is conducted by adding an essentially equimolar amount of a sulfenyl halide, XI, to VII. The reaction is conducted in the liquid phase using an inert anhydrous aprotic organic solvent such as chloroform, methylene chloride, toluene and the like. In some cases the product precipitates from the reaction solution and is purified by filtration followed by air-drying. In those cases in which the product does not precipitate from the reaction solution, the system is washed with an excess of an aqueous basic solution after reaction completion to remove the acid generated during the reaction. Suitable bases which may be employed include for instance sodium carbonate, potassium carbonate, sodium bicarbonate and the like. The reaction is generally conducted at from 0° to 100° C. although preferably at from 20° to 40° C. and is generally complete from within 1 to 72 hours. Reaction pressure is not critical and for convenience the reaction is generally conducted at atmospheric pressure. The product, I(c), is then isolated by conventional procedures such as extraction, filtration, chromatography distillation and the like.

UTILITY

The compounds of this invention are useful for controlling fungi. Some of the compounds of this invention are particularly useful for controlling plant fungal infections caused by *Botrytis cinerea*, leaf blights caused by such organisms as *Phytophthora infestans conidia*, *Alternari solani conidia*, *Septoria apii*, downy mildew caused by organisms such as *Plasmopara viticola* and other fungal infections caused by organisms such as *Pythium ultimum, Rhizoctonia solani, Fusarium moniliforme, Aspergillus niger,* and *Piriculana oryzae.*

However, some fungicidal compounds of the invention may be more fungicidally active than others against particular fungi. Tables II and II(a) list a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, organic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried no relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bacteriocides, plant growth regulators, fertilizers, etc.

Some of the compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, attapulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 0.2 to 60 kg/ha, and the preferred rate is in the range 0.5 to 40 kg/ha.

Some of the compounds of the invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, steams, canals, pools and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep 0.1 to 10 ppm is equal to about 0.3 to 30 pounds per acre of water one foot deep. These compounds may be applied to the aqueous growth environments of such organisms as dispersible powders or in solution with water-miscible solvents.

A further understanding of the invention can be had in the following non-limiting Examples. Wherein, unless expressly stated to the contrary, all temperatures and temperature ranges refer to the Centigrade system and the term "ambient" or "room temperature" refers to about 20° to 25° C. The term "percent" refers to weight percent and the term "mol" or "moles" refers to gram mols. The term "equivalent" refers to a quantity of reagent equal in mols, to the mols of the preceding or succeeding reagent recited in that example in terms of finite mols or finite weight or volume. Also, unless expressly stated to the contrary, E and Z isomers are generated where possible in the reaction and are not separated. Geometric isomer and racemic mixtures are used as starting materials and correspondingly isomers mixtures are obtained as products.

Compounds which were prepared in accordance with Examples 1 to 5 below are listed in Table I.

EXAMPLE 1

Preparation of 2-thio-4,4-diethyl-5-methylenethiazoline

3-Amino-3-ethyl-pentyne, 111.2 gms, was added to 300 ml of carbon tetrachloride. 11.6 gm of pyridine hydrochloride was added and the system stirred for an additional ten minutes. 304.8 gm of carbon disulfide was slowly added to the system. The system was stirred at 41° to 45° C. for 50 hours. At this time, 300 ml of methylene chloride was added. The system was washed with water and the solvent was removed by stripping. The solid was slurried with 400 ml of hexane and filtered. The precipitate was filtered, washed with hexane and air-dried to give the 2-thio-4,4-diethyl-5-methylenethiazoline, 161.3 gm, as an off-white solid, m.p. 107°–109.5° C.

EXAMPLE 2

Preparation of 2-thiocyanomethylthio-4,4-diethyl-5-methylenethiazoline 14.2 gm of sodium hydride (50% in mineral oil) was washed with 4×200 ml of hexane and then added to 400 ml of dimethoxyethane under a nitrogen atmosphere. 63 gm of 2-thio-4,4-diethyl-5-methylenethiazoline in 150 ml of dimethoxyethane was slowly added to the system with evolution of $H_2$ gas. After evolution of $H_2$ gas ceased, the system was stirred for an additional ½ hour at room temperature. The system was then cooled to approximately 15° C. and after cooling, 43.25 gm of chloromethyl thiocyanate was slowly added over 35 minutes. The system was then stirred for approximately 16 hours at room temperature. At this time, the system was filtered and the filtrate washed twice with 50 ml water, then with 50 ml of 5% sodium bicarbonate solution and then with 50 ml of 5% HCl solution. The filtrate was removed by stripping to give 76 gm of the crude product as a brown oil. The crude product was purified by chromatography using 900 gm silica gel. The column was initially run using hexane. The elutant was gradually increased to 40% methylene chloride/hexane. The product was isolated and the solvent removed by stripping to give 56 gm of the 2-thiocyanomethylthio-4,4-diethyl-5-methylenethiazoline. Listed as compound number 6 in Table I.

EXAMPLE 3

Preparation of 2-thiocyanomethylthio-4,4-diethyl-5-E,Z-bromomethylenethiazoline

2-Thiocyanomethylthio-4,4-diethyl-5-methylenethiazoline, 100 gm, was added to 400 ml of dichloromethane under a nitrogen atmosphere. The system was cooled to 15°–20° C. After cooling, 62.3 gm of bromine was slowly added to the system. The system was stirred at room temperature for ½ hour. The system was then washed with a 5% solution of sodium sulfite, then with 1 equivalent of a 5% solution of sodium bicarbonate, and then with 100 ml of water. The dichloromethane was removed by stripping to yield 128 gm of a dark oil. The oil was combined with 400 ml toluene, 40 gm silica gel and 10 gm of charcoal. The mixture was stirred for ½ hour at room temperature, filtered and the toluene removed by stripping. The crude product was purified by column chromatography using silica gel. The column was initially run using 20% methylene chloride/hexane. The elutant was gradually increased to 50% methylene chloride/hexane. The product was isolated and the solvent removed by stripping to give 97.7 gm of the 2-thiocyanomethylthio-4,4-diethyl-5-bromomethylenethiazoline as a mixture of E and Z isomers. Listed as compound number 5 in Table I.

EXAMPLE 4

Preparation of 2-thiocyanomethylthio-4,4-diethyl-5-dichloromethylenethiazoline 2-Thiocyanomethylthio-4,4-diethyl-5-methylenethiazoline, 23. gm, is added to 75 ml of dichloromethane. 0.72 gm of chlorine in 20 ml of dichloromethane is then added to the system. The system is stirred at room temperature for 1 hour. The system is then washed with saturated sodium bicarbonate solution, filtered and the organic solution dried over magnesium sulfate. The dichloromethane is removed by stripping to give the 2-thiocyanomethylthio-4,4-diethyl-5-dichloromethylenethiazoline.

EXAMPLE 5

Preparation of 2-thiocyanomethylthio-4,4-dimethyl-5-(4-chlorophenylthio)methylenethiazoline 2-Thiocyanomethylthio-4,4-dimethyl-5-methylenethiazoline, 4.0 gm (prepared in a manner consistent with Examples 1 and 2) was added to 100 ml of dichloromethane. 3.11 gm of 4-chlorophenylthiochloride was added to the system. The system was stirred at room temperature for 48 hours. The product precipitated from solution. The product was filtered and air-dried to give 4.7 gm of the 2-thiocyanomethylthio-4,4-dimethyl-5-(4-chlorophenylthio)methylenethiazoline as an off-white solid, m.p. 122°–131° C. Listed as compound number 1 in Table I.

Compounds which are prepared in accordance with Examples 1 to 5 include for instance:
2-thiocyanomethylthio-4-ethyl-4-methyl-5-methylenethiazoline;
2-thiocyanomethylthio-4-isopropyl-4-methyl-5-methylenethiazoline;
2-thiocyanomethylthio-4-methyl-4-ethyl-5-bromomethylenethiazoline;
2-thiocyanomethylthio-4,4-dimethyl-5-dichloromethylenethiazoline;
2-thiocyanomethylthio-4,4-diethyl-5-iodomethylenethiazoline;
2-thiocyanomethylthio-4,4-di-n-butyl-5-fluoromethylenethiazoline;
2-thiocyanomethylthio-4,4-di-t-butyl-5-methylthiomethylenethiazoline;
2-thiocyanomethylthio-4,4-diethyl-5-isopropylthiomethylenethiazoline;
2-thiocyanomethylthio-4,4-di-n-propyl-5-phenylthiomethylenethiazoline;
2-thiocyanomethylthio-4,4-diethyl-5-(4-chlorophenylthio)methylenethiazoline;
2-thiocyanomethylthio-4,4-diethyl-5-(4-trifluoromethylphenylthio)methylenethiazoline;
2-thiocyanomethylthio-4,4-dimethyl-5-(4-iodophenylthio)methylenethiazoline;
2-thiocyanomethylthio-4,4-dimethyl-5-(4-bromophenylthio)methylenethiazoline;
2-thiocyanomethylthio-4,4-dimethyl-5-(4-methylphenylthio)methylenethiazoline;
2-thiocyanomethylthio-4,4-di-n-propyl-5-(2,4-dichlorophenylthio)methylenethiazoline;
2-thiocyanomethylthio-4,4-di-sec-butyl-5-(4-nitrophenylthio)methylenethiazoline.

EXAMPLE 6

Mycelial Inhibition

A number of the compounds of the present invention were evaluated for in-vitro fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip. The effectiveness of the compounds tested for fungicidal activity is reported in Table IIa for those compounds which were effective in inhibiting mycelial growth. The activity is reported in terms of $$\frac{\text{micrograms/cm}^2 \text{ for 99\% control of the fungus for test compound}}{\text{micrograms/cm}^2 \text{ for 99\% control of the fungus for standard}} \times 100$$

EXAMPLE 7

Algae and Aquatic Weeds Control

Representative compounds of the invention were tested as aquatic herbicides and algicides by the following method. The weed test species were *Lemna minor, Elodea canadensis* and the algae used was *Spirulina maxima*.

An acetone solution of the test compound and a small amount of an alkylarylpolyoxyethylene glycol-containing surfactant was prepared. This solution was mixed with a nutrient solution in quantity sufficient to give a concentration of 2 ppm. Eight oz. plastic cups were filled with 150 ml of this solution. A sample of the test, Lemna and Elodea, was added together to each cup. Forty ml of Spirulina culture with the 2 ppm treatment was placed in 1½ oz plastic cups (#4 glass vials used after June 9, 1980). The containers were then placed in an illuminated environment maintained at a temperature of about 20° C. for incubation. The containers were observed periodically for growth (as compared to an untreated check). The effectiveness of the test compound was determined based on a final observation of growth after 7 to 10 days. The results of the test on a 0-to-100 basis—0 indicating no effectiveness and 100 indicating complete effectiveness—are reported in Table IV.

EXAMPLE 8

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250 ppm suspension of the test compound in acetone, water and a small amount of a non-ionic emulsifier. The sprayed plants were then inoculated one day later with the organism, placed in an environmental chamber and incubated at 66° to 68° F.

EXAMPLE 9

Celery Late Blight

The celery late blight tests were conducted using celery (Utah) plants 11 weeks old. The celery late blight organism was *Septoria apii*. The celery plants were sprayed with 250 ppm solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation the plants were allowed to dry and then were maintained in a greenhouse for approximately 14 days. The percent disease control provided by a given candidate toxicant is based on the percent disease reduction relative to untreated check plants. The results are reported in Table II.

and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II. In Table II the test concentration is 250 ppm unless otherwise indicated by the figures in parentheses.

EXAMPLE 10

Grape Downy Mildew Control

The compounds of the invention were tested for the control of the grape downy mildew organism *Plasmopara viticola*. Detached leaves, between 70 and 85 mm in diameter, of 7-week old *Vitis vinifera* cultivar Emperor grape seedlings were used as hosts. The leaves were sprayed with a 250 ppm solution of the test compound in acetone. The sprayed leaves were dried, inoculated with a spore suspension of the organism, placed in a humid environmental chamber and incubated at 66° to 68° F. and about 100% relative humidity. After incubation for two days, the plants were then held in a greenhouse seven to nine days; then the amount of disease control was determined. The percent disease control provided by a given gest compound was based on the percent disease reduction relative to untreated check plants. The results are tabulated in Table II.

EXAMPLE 11

Tomato Early Blight

Compounds of the invention were tested for the control of the tomato Early Blight organism, *Alternaria solani conidia*. Tomato (variety Bonny Best) seedlings of 6 to 7 weeks old were used. The tomato plants were sprayed with a 250 ppm solution of the test compound in an acetone-and-water solution containing a small amount of a nonionic emulsifier. The sprayed plants were inoculated one day later with the organism, placed in the environmental chamber and incubated at 66° to 68° F. and 100% relative humidity for 24 hours. Following the incubation, the plants were maintained in a greenhouse for about 12 days. Percent diseases control was based on the percent disease development on untreated check plants. The compounds tested and the results are tabulated in Table II.

EXAMPLE 12

Rice Blast

Compounds of this invention were tested for control of the Rice Blast organism, *Piricularia oryzae*, using 10 to 14-day old rice plant seedlings (Calrose M-9 variety). Seedling plants were sprayed with a 625 ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on untreated check plants:

$$\% \text{ Control} = 100 \times \left( \frac{\% \text{ disease in treated plants}}{\% \text{ disease in check}} \right)$$

The results are tabulated in Table II.

EXAMPLE 13

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of oil and the test solution was sprayed uniformly onto the soil surface at a dose of 33 micrograms/cm². The pot was watered and placed in a greenhouse. The pot was watered intermittently and was observed for seedling emergence, health of emerging seedlings, was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table III.

EXAMPLE 14

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 micrograms/cm². After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table III.

TABLE I

Compounds of the Formula

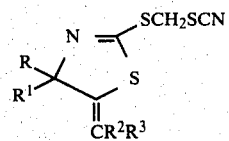

| Compound No. | R | R¹ | R² | R³ | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 1 | $CH_3$ | $CH_3$ | H | $-S-\phi-Cl$ | 45.10 | 42.12 | 3.52 | 3.55 | 7.52 | 7.59 | off-white solid | 122–131° C. |
| 2 | $CH_3$ | $CH_3$ | Cl | Cl | 32.11 | 30.74 | 2.69 | 2.76 | 9.36 | 9.20 | yellow oil | |
| 3 | $CH_3$ | $CH_3$ | H | Cl | 36.28 | 36.24 | 3.42 | 3.69 | 10.58 | 10.54 | yellow solid | 53–59° C. |
| 4 | $CH_3$ | $CH_3$ | H | Br | 31.07 | 31.22 | 2.93 | 2.94 | 9.06 | 9.55 | white solid | 61–63° C. |
| 5 | $C_2H_5$ | $C_2H_5$ | H | Br | 35.62 | 35.88 | 3.89 | 4.08 | 8.31 | 8.35 | yellow oil | |
| 6 | $C_2H_5$ | $C_2H_5$ | H | H | 46.50 | 46.73 | 5.46 | 5.54 | 10.85 | 11.24 | yellow oil | |
| 7 | $CH_3$ | $CH_3$ | H | H | 41.71 | 40.46 | 4.38 | 4.50 | 12.16 | 13.35 | yellow oil | |
| 8 | (cyclopentyl) | | H | H | — | — | — | — | — | — | white solid | 81–85° C. |

TABLE II

Fungicidal Activity % Control

| Compound Number | Grape D.M. | Tom. L. Bl. | Cel. L. Bl. | Tom. E. Bl. | Rice Blast |
|---|---|---|---|---|---|
| 1 | 100 | 21 | 70 | 47 | — |
| 2 | 88 | 0 | 35 | 67 | — |
| 3 | 79 | 21 | 15 | — | — |
| 4 | 100 | 0 | 23 | — | — |
| 5 | 100 | 20 | 96 | 0 | 90 |
| 6 | 0 | 0 | 0 | 0 | — |
| 7 | 50 | 75 | — | 71 | — |
| 8 | 100 | 29 | — | 0 | — |

Grape D.M. — Grape Downy Mildew (*Plasmopara viticola*)
Tom. L. Bl. — Tomato Late Blight (*Phytophthora infestans*)
Tom. E. Bl. — Tomato Early Blight (*Alternaria solani condida*)
Cel. L. Bl. — Celery Late Blight (*Septoria apii*)
Rice Blast (*Piriculana oryzae*)

TABLE II(a)

Fungicidal Activity (Mycelial Inhibition) % Standard[1]

| Compound Number | Pythium | Rhizoc. | Fusarium | Botrytis | Asper. |
|---|---|---|---|---|---|
| 1 | — | 0 | 0 | 0 | 0 |
| 2 | — | 71 | 29 | 32 | 107 |
| 3 | 40 | 55 | 115 | 64 | 69 |
| 4 | 14 | 92 | 77 | 36 | 63 |
| 5 | 0 | 82 | 0 | 0 | 50 |
| 6 | 31 | 89 | 31 | 30 | 77 |
| 7 | 55 | 39 | 32 | 82 | 32 |
| 8 | 0 | 71 | 0 | 26 | 77 |

[1]Standard = DIFOLATAN ®
Pythium - *Pythium Ultimum*
Rhizoc. - *Rhizoctonia solani*
Asper. - *Aspergillus Niger*
Fusarium - *Fusarium Moniliforme*
Botrytis - *Botrytis Cineria*

TABLE III

Herbicidal Activity Pre-Emergence/Post-Emergence % Control

| Compound Number | L'Qtr. | Mustard | Pigweed | Crabgrass | Watergrass | Soybean |
|---|---|---|---|---|---|---|
| 1 | — | — | — | — | — | — |
| 2 | 0/40 | 0/63 | 0/55 | 0/25 | 0/45 | 0/10 |
| 3 | 25/0 | 15/0 | 35/0 | — | — | — |
| 4 | — | — | — | — | — | — |
| 5 | 0/33 | 0/35 | 0/35 | 0/30 | 0/58 | 0/20 |
| 6 | 73/55 | 58/35 | 73/35 | 0/45 | 0/35 | 30/15 |
| 7 | 60/55 | 0/50 | 50/35 | 0/35 | 0/22 | 45/0 |
| 8 | 0/40 | 0/25 | 0/50 | 0/20 | 0/38 | 0/33 |

— = 0/0
L'Qtr = Lambsquarter (*Chenopodium album*)
Mustard = *Brassica arvensis*
Pigweed = *Amaranthus retraflexus*
Crabgrass = *Digitaria sanguinalis*
Watergrass = *Ethinochloa crusgalli*

TABLE IV

Algicidal Activity % Control

| Compound Number | Spirulina | Lemna | Elodea |
|---|---|---|---|
| 1 | 0 | 0 | 0 |
| 2 | 45 | 50 | 70 |
| 3 | 40 | 40 | 90 |
| 4 | 30 | 35 | 80 |
| 5 | 40 | 0 | 55 |
| 6 | 75 | 0 | 0 |
| 7 | 90 | 90 | 85 |
| 8 | 70 | 60 | 80 |

Spirulina - *Spirulina maxima*
Lemna - *Lemna minor*
Elodea - *Elodea Canadensis*

I claim:
1. A compound of the formula

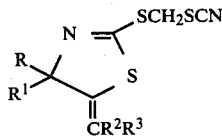

wherein R and $R^1$ are independently lower alkyl or R and $R^1$ are joined to form a cycloalkyl group of 5 to 8 carbon atoms; $R^2$ is hydrogen or chloro; and $R^3$ is hydrogen, halogen or $-SR^4$ wherein $R^4$ is lower alkyl, phenyl or phenyl substituted with 1 to 3 of the same or different substituents selected from halogen, nitro, lower alkyl or lower alkyl substituted with 1 to 3 halogens with the proviso that when $R^2$ is chloro, $R^3$ is not $-SR^4$, bromine, fluorine or iodine.

2. A compound of the formula defined in claim 1 wherein R and $R^1$ are both methyl.

3. A compound of the formula defined in claim 1 wherein R and $R^1$ are joined to form cyclohexyl.

4. A compound of the formula defined in claim 1 wherein R and $R^1$ are both ethyl.

5. A compound of the formula defined in claim 1 wherein $R^2$ is hydrogen and $R^3$ is bromo.

6. A compound of the formula defined in claim 4 wherein $R^2$ is hydrogen and $R^3$ is bromo.

7. A compound of the formula defined in claim 1 wherein $R^3$ is hydrogen or halogen.

8. A method for the control of fungi which comprises applying thereto a fungicidally effective amount of the compound defined in claim 1.

9. A method for the control of fungi which comprises applying thereto a fungicidally effective amount of the compound defined in claim 6.

10. A fungicidal composition comprising a biologically inert carrier and a fungicidally effective amount of a compound of the formula defined in claim 1.

11. A fungicidal composition comprising a biologically inert carrier and a fungicidally effective amount of a compound of the formula defined in claim 6.

12. A method for the control of algae which comprises applying thereto an algicidally effective amount of a compound of the formula defined in claim 7.

13. An algicidal composition comprising a biologically inert carrier and an algicidally effective amount of the compound defined in claim 7.

14. A method for controlling undesired vegetation which comprises applying to said vegetation or its growth medium a herbicidally effective amount of the compound defined in claim 7 with the proviso that when R and $R^1$ are methyl and $R^2$ is hydrogen, $R^3$ is not bromo.

15. A herbicidal composition comprising a herbicidally effective amount of a compound defined in claim 7 and a biologically inert carrier with the proviso that when R and $R^1$ are methyl and $R^2$ is hydrogen, $R^3$ is not bromo.

* * * * *